(12) United States Patent
Rollow, IV

(10) Patent No.: US 10,972,835 B2
(45) Date of Patent: Apr. 6, 2021

(54) CONFERENCE SYSTEM WITH A MICROPHONE ARRAY SYSTEM AND A METHOD OF SPEECH ACQUISITION IN A CONFERENCE SYSTEM

(71) Applicant: Sennheiser electronic GmbH & Co. KG, Wedemark (DE)

(72) Inventor: J. Douglas Rollow, IV, San Francisco, CA (US)

(73) Assignee: Sennheiser electronic GmbH & Co. KG, Wedemark (DE)

(*) Notice: Subject to any disclaimer, the term of this patent is extended or adjusted under 35 U.S.C. 154(b) by 0 days.

(21) Appl. No.: 16/541,521

(22) Filed: Aug. 15, 2019

(65) Prior Publication Data

US 2020/0145753 A1 May 7, 2020

Related U.S. Application Data

(60) Provisional application No. 62/754,272, filed on Nov. 1, 2018.

(51) Int. Cl.
*H04R 3/00* (2006.01)
*A61B 5/00* (2006.01)
*H04L 12/18* (2006.01)
*H04R 1/40* (2006.01)

(52) U.S. Cl.
CPC ............ *H04R 3/005* (2013.01); *A61B 5/746* (2013.01); *H04L 12/1822* (2013.01); *H04R 1/406* (2013.01); *A61B 5/0022* (2013.01)

(58) Field of Classification Search
CPC ..... H04R 3/005; H04R 1/406; H04L 12/1822; H04S 7/302; H04S 7/303; H04S 7/304; H04S 2420/01; H04S 2400/11; H04S 2400/15
See application file for complete search history.

(56) References Cited

U.S. PATENT DOCUMENTS

| 6,731,334 | B1 | 5/2004 | Maeng et al. |
| 7,116,787 | B2 * | 10/2006 | Faller ..................... H04M 3/56 |
| | | | 381/17 |
| 9,560,446 | B1 * | 1/2017 | Chang .................... H04R 3/005 |
| 9,894,434 | B2 | 2/2018 | Roll, IV et al. |
| 10,504,529 | B2 * | 12/2019 | Sun ........................ H04S 7/304 |
| 2008/0247567 | A1 | 10/2008 | Kjolerbakken et al. |

(Continued)

*Primary Examiner* — Kile O Blair
(74) *Attorney, Agent, or Firm* — Haug Partners LLP

(57) ABSTRACT

A conference system with transmitting and receiving sides. The transmitting side has a microphone array unit with microphone capsules, and a processing unit. The processing unit is configured to receive output signals of the microphone capsules and to execute audio beamforming based on the received output signals for acquiring sound coming from an audio source in a first direction. The processing unit has a direction-recognition unit that computes from the output signals of said microphone capsules a score for each of multiple search grid spatial positions and uses a search grid spatial position having a higher score to identify said first direction. The receiving side has an audio reproduction system that reproduces an audio signal detected by the microphone array with directional information of the first direction. The detected audio signal and the directional information regarding the first direction are transmitted from the transmitting side to the receiving side.

33 Claims, 7 Drawing Sheets

(56) References Cited

U.S. PATENT DOCUMENTS

| | | | |
|---|---|---|---|
| 2011/0033063 A1* | 2/2011 | McGrath | H04S 7/30 381/92 |
| 2013/0321566 A1* | 12/2013 | Simonnet | H04N 7/142 348/14.16 |
| 2016/0094929 A1* | 3/2016 | Brannmark | H04S 7/303 381/310 |
| 2017/0134849 A1* | 5/2017 | Pandey | G10L 21/0264 |

* cited by examiner

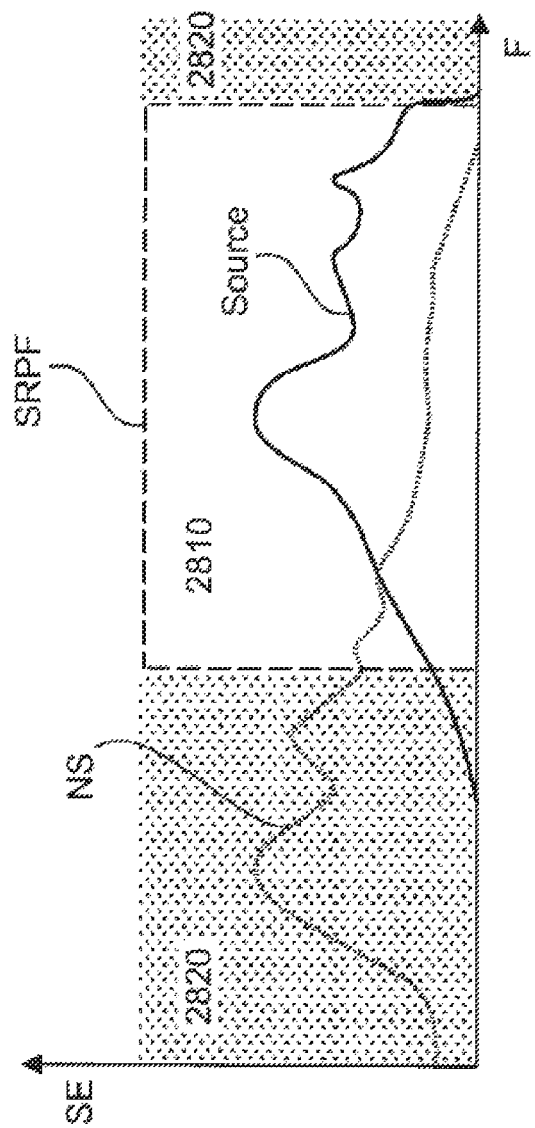

CONFERENCE SYSTEM WITH A MICROPHONE ARRAY SYSTEM AND A METHOD OF SPEECH ACQUISITION IN A CONFERENCE SYSTEM

The present application claims priority from U.S. Provisional Patent Application Ser. No. 62/754,272 filed on Nov. 1, 2018, the disclosure of which is incorporated herein by reference in its entirety.

FIELD OF THE INVENTION

It is noted that citation or identification of any document in this application is not an admission that such document is available as prior art to the present invention.

The invention relates to a conference system as well as a method of speech acquisition in a conference system.

In a conference system, the speech signal of one or more participants, typically located in a conference room, must be acquired such that it can be transmitted to remote participants or for local replay, recording or other processing.

FIG. 1A shows a schematic representation of a first conference environment as known from the prior art. The participants of the conference are sitting at a table 1020 and a microphone 1100 is arranged in front of each participant 1010. The conference room 1001 may be equipped with some disturbing sound source 1200 as depicted on the right side. This may be some kind of fan cooled device like a projector or some other technical device producing noise. In many cases those noise sources are permanently installed at a certain place in the room 1001.

Each microphone 1100 may have a suitable directivity pattern, e.g. cardioid, and is directed to the mouth of the corresponding participant 1010. This arrangement enables predominant acquisition of the participants' 1010 speech and reduced acquisition of disturbing noise. The microphone signals from the different participants 1010 may be summed together and can be transmitted to remote participants. A disadvantage of this solution is the microphone 1100 requiring space on the table 1020, thereby restricting the participants' work space. Furthermore, for proper speech acquisition, the participants 1010 have to stay at their seat. If a participant 1010 walks around in the room 1001, e.g. for using a whiteboard for additional explanation, this arrangement leads to degraded speech acquisition results.

FIG. 1B shows a schematic representation of a similar conference environment according to the prior art. Instead of using one installed microphone for each participant, one or more microphones 1110 are arranged for acquiring sound from the whole room 1001. Therefore, the microphone 1110 may have an omnidirectional directivity pattern. It may either be located on the conference table 1020 or e.g. ceiling mounted above the table 1020 as shown in FIG. 1B. The advantage of this arrangement is the free space on the table 1020. Furthermore, the participants 1010 may walk around in the room 1001 and as long as they stay close to the microphone 1110, the speech acquisition quality remains at a certain level. On the other hand, in this arrangement disturbing noise is always fully included in the acquired audio signal. Furthermore, the omnidirectional directivity pattern results in noticeable signal to noise level degradation at increased distance from the speaker to the microphone.

FIG. 1C shows a schematic representation of a further conference environment according to the prior art. Here, each participant 1010 is wearing a head mounted microphone 1120. This enables a predominant acquisition of the participants' speech and reduced acquisition of disturbing noise, thereby providing the benefits of the solution from FIG. 1A. At the same time the space on the table 1020 remains free and the participants 1010 can walk around in the room 1001 as known from the solution of FIG. 1B. A significant disadvantage of this third solution consist in a protracted setup procedure for equipping every participant with a microphone and for connecting the microphones to the conference system.

US 2008/0247567 A1 shows a two-dimensional microphone array for creating an audio beam pointing to a given direction.

U.S. Pat. No. 6,731,334 B1 shows a microphone array used for tracking the position of a speaking person for steering a camera.

U.S. Pat. No. 9,894,434 B2 discloses a conference system, comprising: a microphone array unit having a plurality of microphone capsules arranged in or on a board mountable on or in a ceiling of a conference room. The microphone array unit has a steerable beam and a maximum detection angle range. The conference system comprises a processing unit which is configured to receive the output signals of the microphone capsules and to steer the beam based on the received output signal of the microphone array unit. The processing unit is configured to control the microphone array to limit the detection angle range to exclude at least one predetermined exclusion sector in which a noise source is located.

SUMMARY OF THE INVENTION

It is an object of the invention to provide a conference system that enables enhanced freedom of the participants at improved speech acquisition and reduced setup effort as well as an improved audio reproduction at a receiving side.

This object is solved by a conference system comprising, at a transmitting side, a microphone array unit having a plurality of microphone capsules arranged in or on a board mountable on or in a ceiling of a conference room and a processing unit which is configured to receive output signals of the microphone capsules and to execute audio beamforming based on the received output signals of the microphone capsules for predominantly acquiring sound coming from an audio source in a first direction. The processing unit comprises a direction recognition unit which is configured to compute from the output signals of the microphone capsules a score for each of a plurality of spatial positions on a search grid and to use a search grid position having a higher or highest score to identify said first direction. At a receiving side, an audio reproduction system is provided and is configured to reproduce an audio signal detected by the microphone unit with directional information of the first direction. The audio signal detected by the microphone capsule as well as a directional information regarding the first direction is transmitted from the transmitting side to the receiving side.

According to an aspect of the invention, an isolated signal of the speaker can be detected by the microphone array in a conference room using beamforming. Furthermore, spatial information regarding the position of the speaker can also be detected by the microphone array. The isolated audio signal as well as the spatial information can be transmitted to a receiving side where the isolated signal and the spatial information can be used to create an augmented (so-called hyper-realistic), spatial audio impression. Accordingly, an immersive audio experience can be provided at the receiving side. Furthermore, this technique is also advantageous as it increases the intelligibility of the audio conference.

According to an aspect of the invention, a ceiling microphone array is used to detect an audio signal from a speaker by using beamforming, and to detect the direction of the audio signal from the speaker. The detected audio signal as well as the spatial information (directional information) is transmitted to a receiving side. At the receiving side, the audio signal together with the spatial information or directional information can be used to create a spatial audio impression. Accordingly, a remote participant of a conference can hear different people speaking from the same directions as in the original conference room.

According to an aspect of the invention, the spatial audio impression for the remote participant can be generated in particular with a headphone having a head tracker. By using binaural rendering techniques including head related transfer function, the impression of sound coming from different directions can be achieved at the receiving side. The conference system according to the invention is advantageous as a remote participant in the conference (at the receiving side) can have the impression of acoustically being in the conference room at the transmitting side. By using the beamforming, it is possible that the user at the receiving side only hears the audio signal from the speaking person without environmental noise. The environmental noise can be cancelled by means of the beamforming. The receiving side can be in the same conference room as the transmitting side or can be in a remote conference room.

Preferably, the audio signal as well as the spatial or directional information is digitally transmitted.

BRIEF DESCRIPTION OF THE DRAWINGS

Advantages and embodiments of the invention are elucidated by the following figures.

FIG. 8 shows a graph indicating a relation between a spectral energy SE and the frequency F.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1A:
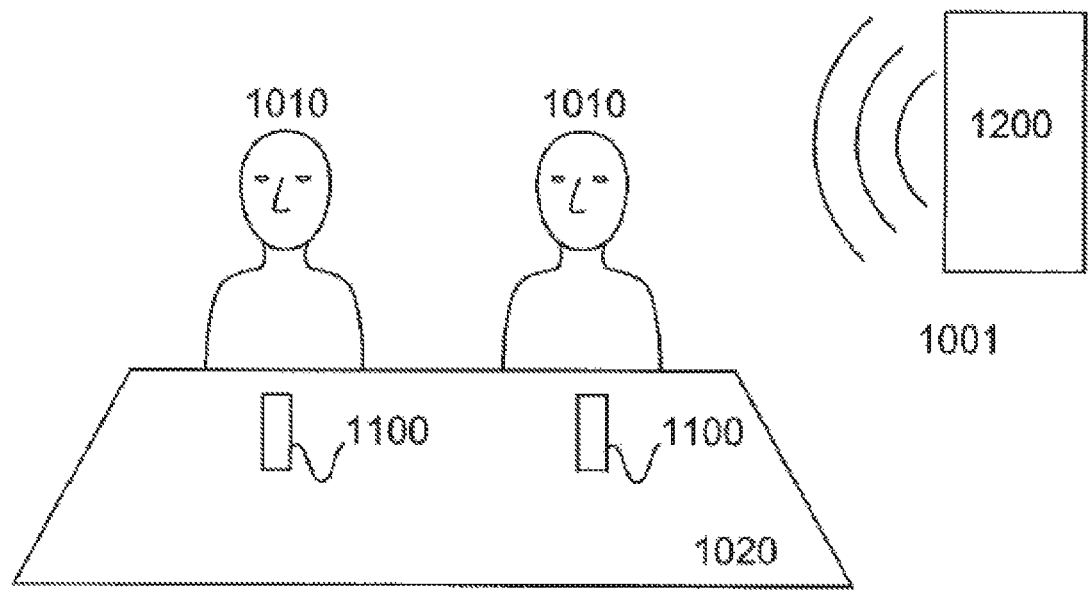
FIG. 1A shows a schematic representation of a first conference environment as known from the prior art.
Figure 1B:
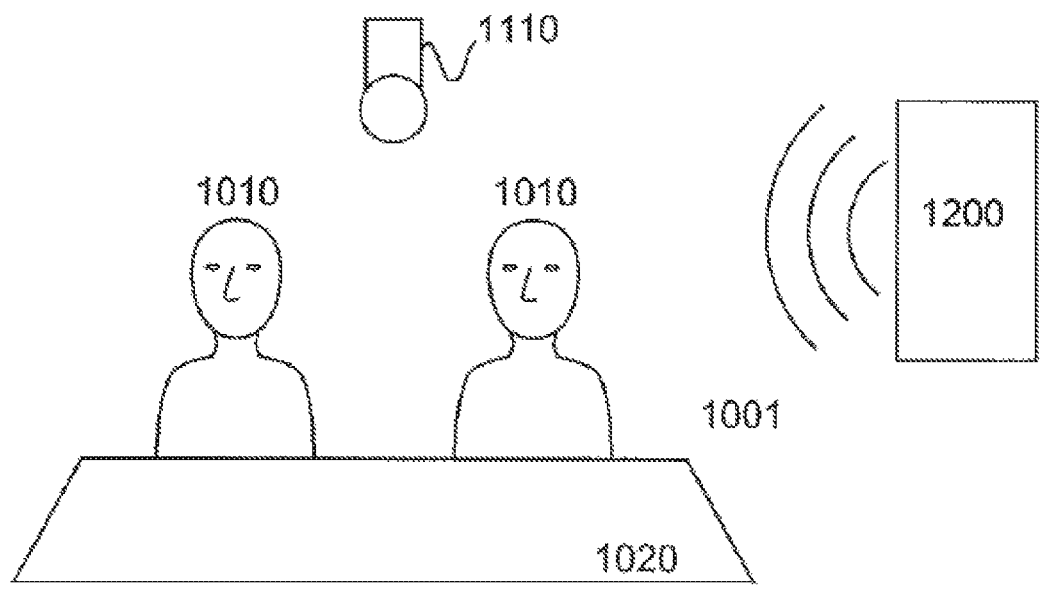
FIG. 1B shows a schematic representation of a second conference environment according to the prior art.
Figure 1C:
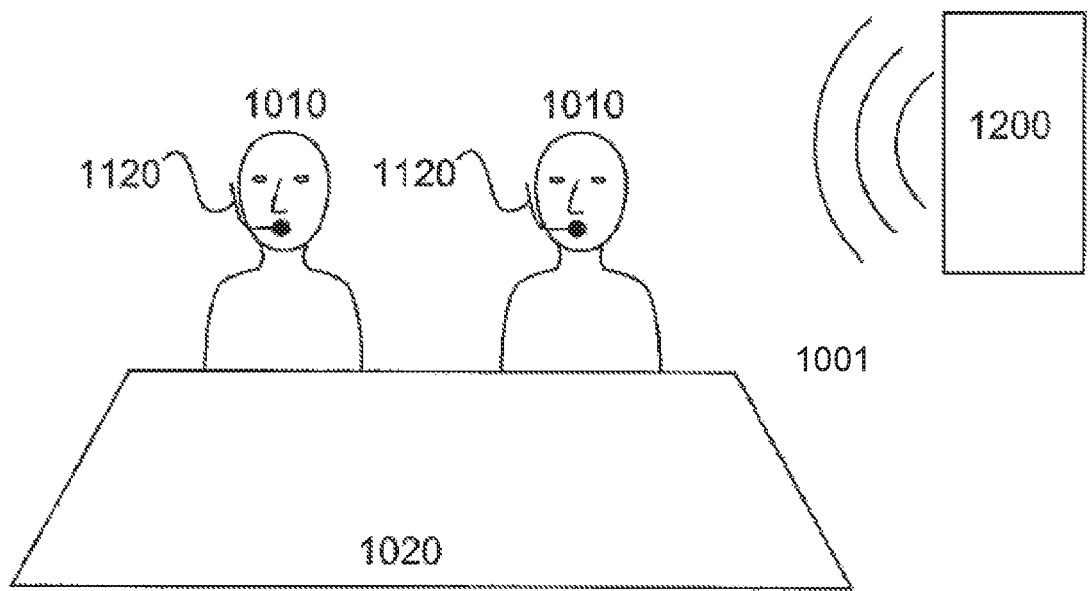
FIG. 1C shows a schematic representation of a further conference environment according to the prior art.
Figure 2:
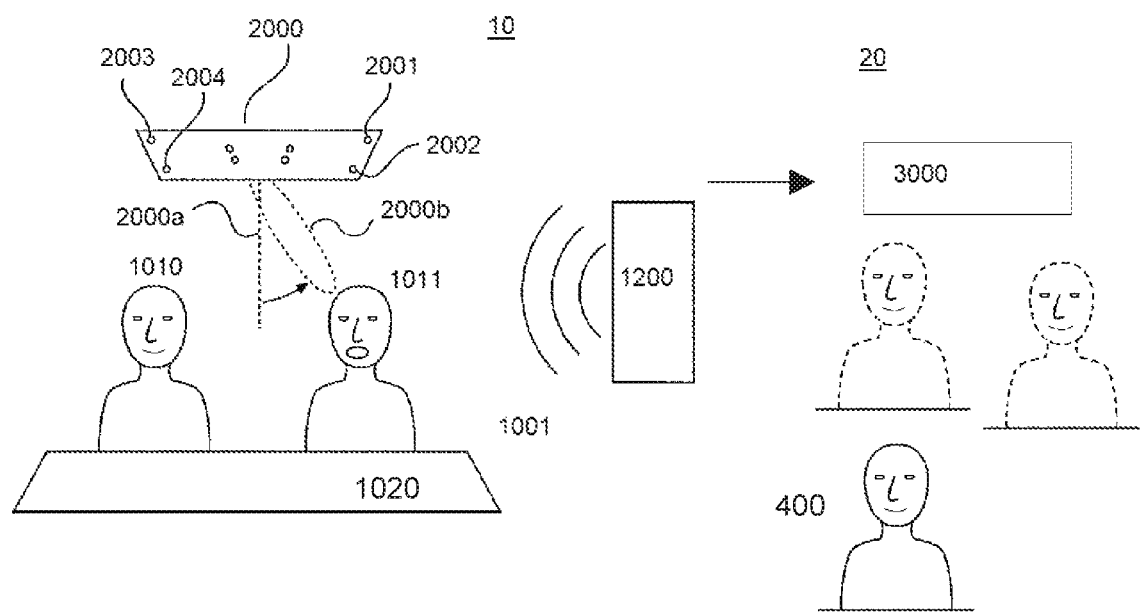
FIG. 2 shows a schematic representation of a conference system according to the invention.

FIG. 2 shows a schematic representation of a conference system according to the invention. The conference system comprises a transmitting side 10 and a receiving side 20. At the transmitting side 10, a microphone array 2000 can be mounted above the conference table 1020 or rather above the participants 1010, 1011 in a conference room or venue 1001. The microphone array unit 2000 is thus preferably ceiling mounted. The microphone array 2000 comprises a plurality of microphone capsules 2001-2004 preferably arranged in a two-dimensional configuration. The microphone array has an axis 2000a and can perform audio beamforming having a beam 2000b. The microphone array 2000 serves to detect sound from the conference room or venue 1001 and in particular sound from at least one speaker in the conference room.

The audio signals acquired by the microphone capsules 2001-2004 are fed to a processing unit 2400 (shown in FIG. 4) of the microphone array unit 2000. Based on the output signals of the microphone capsules, the processing unit 2400 identifies the direction in which a speaking person is located. The direction may be identified, e.g., by a spherical angle relating to the microphone array, which may include a polar angle and an azimuth angle, and optionally a radial distance. The processing unit 2400 then executes audio beamforming to obtain an audio beam 2000b based on the microphone capsules' signals for predominantly acquiring sound coming from the direction as identified.

The signals as detected by the microphone array 2000, i.e. the audio signal as well as a directional signal indicating the direction of the audio signal, are transmitted to a receiving side 20. At the receiving side 20, at least one participant 400 of a conference call is located in a second venue, such as a conference room or conference venue. Furthermore, an audio reproduction system 3000 is provided in the second venue to reproduce the audio received from the transmitting side. The audio as received at the receiving side is preferably reproduced as immersive audio including the audio signal as well as the directional information as transmitted from the transmitting side 10. In particular, an audio signal with spatial information is rendered. Accordingly, the participant 400 can participate in the conference call, wherein the sound from the transmitting side 10 is reproduced by the audio reproduction system 3000 with directional or spatial information. Accordingly, the participant 400 at the receiving side will receive the audio signal with a direction sense, i.e. the participant 400 will have the impression that the audio reproduced by the audio reproduction system 3000 is coming from a direction in which a current speaker 11 at the transmitting side 10 is positioned.

Hence, the detected audio signal (e.g. of a speaker as detected by using beamforming) as well as directional information is transmitted from the transmitting side 10 to the receiving side 20 to enable a spatial audio processing allowing an immersive audio reproduction.

The receiving side 20 may be remote from the transmitting side 10. Alternatively, it is also possible that the receiving side 20 is located near or in the conference venue of the transmitting side 10. This can for example be the case if the participant 400 is wearing a headset. In this case, a participant being e.g. in a large conference hall and wearing headphones may listen via the headset to other participants who are in the same conference hall. According to the invention, the audio signal that is replayed to the participant through the headset is rendered as a spatial audio signal according to the directional information. Consequently, the listening participant can easier identify a current speaker's position, relative to a reference position or relative to the listener's own position. For this, the listener's position and/or head orientation may be determined, which may happen dynamically or statically. Various optical, acoustical or other methods are known and may be utilized to determine the listener's position. For example, each seat in the conference hall may provide positional information, which may be used to configure the respective participant's headset. The headset may automatically detect this positional information and render the received audio and directional signals respectively, relative to its current position. Further, the headset may comprise a head tracker for determining the listener's head orientation.

With the conference system according to the invention, it is possible to allow a spatial audio impression for a participant at the receiving side 20 which may be remote from the transmitting side 10. As another example, a participant at the remote receiving side 20 of the conference can hear different persons speaking from their respective direction, as if the participant were in the conference room at the transmitting side 10. Hence, a remote participant has an immersive audio impression giving him the feeling of being acoustically at the conference room at the transmitting side. Optionally, as the audio signal detected by the microphone array is based on audio beamforming, the quality of the audio signal detected by the microphone array can be improved. Advantageously, environmental noise can be reduced if the full capabilities of the beamforming of the microphone array is used.

With the conference system according to the invention, a virtual audio teleconferencing is possible, wherein a participant at a remote location can have an immersive audio experience.

The direction of a currently speaking person can periodically be re-identified and the direction of the microphone beam 2000b can be continuously adjusted accordingly. The whole system can be pre-installed in a conference room and pre-configured, so that no particular initial setup procedure is needed for preparing the speech acquisition. At the same time, tracing the speaking person is possible and enables a predominant acquisition of the participants' speech as well as a reduced acquisition of disturbing noise. Furthermore, the space on the table remains free and the participants can walk around in the room at constant speech acquisition quality.

Figure 3:
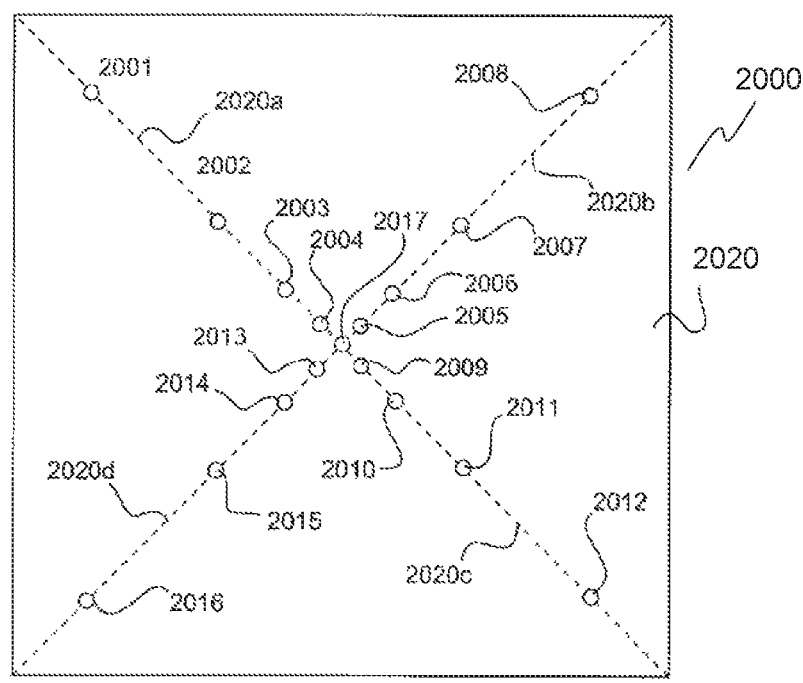
FIG. 3 shows a schematic representation of a microphone array according to the invention.

FIG. 3 shows a schematic representation of a microphone array unit according to the invention, in one embodiment. The microphone array 2000 consists of a plurality of microphone capsules 2001-2017 and a (flat) carrier board 2020. The carrier board 2020 features a closed plane surface that may be larger than 30 cm×30 cm in size. The capsules 2001-2017 are preferably arranged in a two-dimensional configuration on one side of the surface in close distance to the surface, e.g. with less than 3 cm distance between the capsule entrance and the surface. Optionally, the capsules 2001-2017 are inserted into the carrier board 2020 for enabling a zero distance to the surface. The carrier board 2020 is closed in such a way that sound can reach the capsules from the surface side, but sound is blocked away from the capsules from the opposite side by the closed carrier board. This is advantageous as it prevents the capsules from acquiring reflected sound coming from a direction opposite to the surface side. Furthermore, the surface provides a 6 dB pressure gain due to the reflection at the surface and thus increased signal to noise ratio.

The carrier board 2020 can optionally have a square shape. Preferably it is mounted to the ceiling in a conference room in a way that the surface is arranged in a substantially horizontal orientation. On the surface directing down from the ceiling, the microphone capsules are arranged. FIG. 3 shows a plane view of the microphone surface side of the carrier board (from the direction facing the room).

Here, the capsules are arranged on the diagonals of the square shape. There are four connection lines 2020a-2020d, each starting at the midpoint of the square and ending at one of the four edges of the square. Along each of those four lines 2020a-2020d, a number of microphone capsules 2001-2017 is arranged in a common distance pattern. Starting at the midpoint, the distance between two neighboring capsules along the line is increasing with increasing distance from the midpoint. In one embodiment, the distance pattern represents a logarithmic function with the distance to the midpoint as argument and the distance between two neighboring capsules as function value. Optionally, a number of microphones which are placed close to the center have an equidistant linear spacing, resulting in an overall linear-logarithmic distribution of microphone capsules.

The outermost capsule (close to the edge) 2001, 2008, 2016, 2012 on each connection line still keeps a distance to the edge of the square shape (at least the same distance as the distance between the two innermost capsules). This enables the carrier board to also block away reflected sound from the outermost capsules and reduces artifacts due to edge diffraction if the carrier board is not flush mounted into the ceiling.

Optionally, the microphone array further comprises a cover for covering the microphone surface side of the carrier board and the microphone capsules. The cover preferably is designed to be acoustically transparent, so that the cover does not have a substantial impact on the sound reaching the microphone capsules.

Preferably, all microphone capsules are of the same type, so that they all feature the same frequency response and the same directivity pattern. The preferred directivity pattern for the microphone capsules 2001-2017 is omnidirectional as this provides as close as possible a sound incident angle independent frequency response for the individual microphone capsules. However, other directivity patterns are possible.

Specifically, cardioid pattern microphone capsules can be used to achieve better directivity, especially at low frequencies. The capsules are preferably arranged mechanically parallel to each other in the sense that the directivity pattern of the capsules all point into the same direction. This is advantageous as it enables the same frequency response for all capsules at a given sound incidence direction, especially with respect to the phase response.

In situations where the microphone system is not flush mounted in the ceiling, further optional designs are possible.

Figure 4:
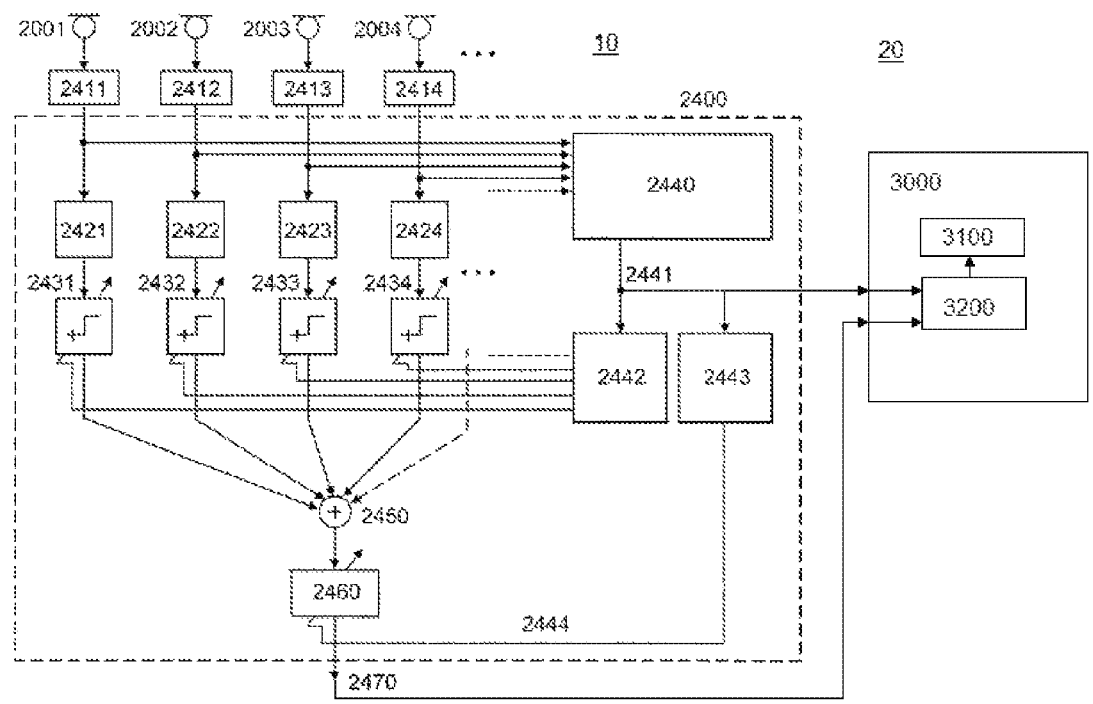
FIG. 4 shows a block diagram of a conference system according to the invention.

FIG. 4 shows a block diagram of a conference system, and in particular a processing unit of a microphone array unit, according to the invention. The audio signals acquired by the microphone capsules 2001-2017 are fed to the processing unit 2400. Although in FIG. 4 only four microphone capsules 2001-2004 are depicted, these stand as placeholder for the complete plurality of microphone capsules of the microphone array. A corresponding signal path for each microphone capsule is provided in the processing unit 2400. The audio signals acquired by the capsules 2001-2004 are each fed to a corresponding analog/digital converter 2411-2414. Inside the processing unit 2400, the digital audio signals from the converters 2411-2414 are provided to a direction recognition unit 2440. The direction recognition unit 2440 identifies the direction in which a speaking person is located as seen from the microphone array 2000 and outputs this information as direction signal or directional information or spatial information 2441. The direction information 2441 may e.g. be provided in Cartesian coordinates or in spherical coordinates including an elevation angle and an azimuth angle. Furthermore, the distance to the speaking person may also be provided as part of the direction signal or the directional information 2441.

The processing unit 2400 furthermore comprises individual filters 2421-2424 for each microphone signal. The output of each individual filters 2421-2424 is fed to an individual delay unit 2431-2434 for individually adding an adjustable delay to each of those signals. The outputs of all those delay units 2431-2434 are summed together in a summing unit 2450. The output of the summing unit 2450 may be fed to an optional frequency response correction filter 2460. The output signal of the summing unit 2450 or the output signal of the frequency response correction filter 2460 represents the overall output signal 2470 of the processing unit 2400. This is the signal representing a speaking person's voice signal coming from the identified direction. The processing unit 2400 may be implemented by one or more microprocessors that may be configured accordingly by software.

Directing the audio beam to the direction as identified by the direction recognition unit 2440 in the embodiment of FIG. 4 can optionally be implemented in a "delay and sum" approach by the delay units 2431-2434. The processing unit 2400 therefore includes a delay control unit 2442 for receiving the direction information 2441 and for converting it into delay values for the delay units 2431-2434. The delay units 2431-2434 are configured to receive those delay values and to adjust their delay time accordingly.

In the current embodiment, the processing unit 2400 furthermore comprises an optional correction control unit 2443. The correction control unit 2443 receives the direction information 2441 from the direction recognition unit 2440 and converts it into a correction control signal 2444. The correction control signal 2444 is used to adjust the optional frequency response correction filter 2460. The frequency response correction filter 2460 can be performed as an adjustable equalizing unit. The setting of this equalizing unit is based on the finding that the frequency response as observed from the speaking person's voice signal to the output of the summing unit 2450 is dependent from the direction the audio beam 2000*b* is directed to. Therefore, the frequency response correction filter 2460 is configured to compensate deviations from a desired amplitude frequency response by a filter 2460 having an inverted amplitude frequency response.

The direction recognition unit 2440 may also be implemented as a position recognition unit, as it detects the position of audio sources by processing the digitized signals of at least two of the microphone capsules as depicted in FIG. 4. This task can be achieved by several algorithms. In one embodiment, the SRP-PHAT (Steered Response Power with PHAse Transform) algorithm is used, as known from prior art.

At the receiving side 20, an audio reproduction system 3000 is provided. The audio reproduction system 3000 comprises a plurality of speakers 3100. The plurality of speakers 3100 can be implemented e.g. as a headphone with two speakers. The audio reproduction system 3000 furthermore comprises a binaural rendering engine 3200 which receives the audio signal 2470 as well as the directional information 2441 and creates a spatial audio signal which can be reproduced by the plurality of speakers 3100. The binaural rendering engine 3200 is used to render at the receiving side 20 an audio signal at a virtual audio source position that corresponds to a speaker's position in the conference room 1001. Hence, the remote participant at the receiving side 20 experiences an audio environment in which each conference participant within the conference room 1001 at the transmitting side 10 is placed at his or her individual location. Advantageously, this can be achieved even though only a single audio channel including the audio signal 2470 from the microphone array is transmitted from the transmitting side 10 to the receiving side 20. Together with this audio signal 2470, also the directional information 2441 is transmitted, for example as a synchronous metadata stream. The metadata stream including the directional information 2441 can be, for example, a continuous stream enabling a specification of updated locations of the participants or talkers in the conference room at the transmitting side.

The binaural rendering engine 3200 can be able to create a virtual environment by means of the plurality of speakers with a static reassigned reverberation. The reverberation can be a simulated reverb e.g. of the conference room 1001 where the audio was recorded, or it can be a reverberation of the room where the participant at the receiving side 20 is. This can be advantageous, as the remote participant can have the feeling of being in the same room as the other participant.

This directional signal or directional information 2441 is transmitted together with the detected audio signal from the transmitting side 10 to the receiving side 20, where the detected audio signal can be reproduced as a spatial audio signal for an immersive audio experience. The directional information 2441 is used to create the spatial and immersive audio impression such that a participant at the remote location perceives the same audio experience as a person in the conference room 1001 at the transmitting side 10.

As the audio signal in the conference room 1001 at the transmitting side 10 is detected by a microphone array having a plurality of microphone capsules, a binaural recording of the audio signals in the conference room is possible. As these binaurally recorded audio signals are transmitted together with the directional information, an immersive conference experience is possible. Accordingly, the participants at the conference room 1001 as well as remote participants can have the feeling that they are in the same room as the participants at the transmitting side 10. By using beamforming, environmental noise can be removed from the detected audio signal such that the overall audio quality can be significantly improved.

The immersive audio experience can be improved for example if a participant uses headphones in particular with head tracking capability.

The immersive audio conferencing according to the invention can be achieved by using spatial audio processing with the detected audio signal as well as the directional information.

Due to the beamforming capabilities of the microphone array 2000, a spatial audio sensing is possible.

According to an aspect of the invention, the directional information 2441 can be represented by a location vector, for example like a directional vector. Accordingly, in this case the true distance from the talker at the transmitting side 10 to the microphone array 2000 is not detected or analyzed. In other words, the directional information can include just a location vector enabling a beamforming based on the spatial direction but not the distance between the conference participant and the microphone array.

According to an aspect of the invention, a virtual location of a participant in the conference room 1001 at the transmitting side 10 can be computed by determining an intersection of the position vector with a plane at a specified height in the conference room. This will lead to a single point in the plane defining the speaker's position. This point can be used by the binaural rendering engine 3200 for a corresponding binaural rendering, so that all conference room participants appear at the same height in the virtual space at the receiving side 20. This has the advantage that only two coordinates need to be transmitted, since the plane has only two dimensions. Hence, only azimuthal tracking is required to render the virtual acoustic locations of the participants or talkers in the conference room 1001 at the transmitting side 10.

According to an aspect of the invention, reverberation parameters at the transmitting side 10 and/or at the receiving side 20 can be measured offline and can be provided to the binaural rendering engine 3200 as a set of static configuration parameters. Moreover, network and software latency parameters can be measured before the conference. A histogram of position update latency can be used to determine a single overall latency which is applied to the audio signal such that it is in accordance with geometry updates.

According to a further aspect of the invention, directional information 2411 can be transmitted in form of a metadata stream. Alternatively, the binaural rendering engine 3200 may use a polling technique to receive the latest geometry information upon request. This is easy to implement as existing ceiling microphone arrays can be used. If necessary, they may be easily adapted by an additional polling interface. The microphone array unit may have an input for receiving such requests and provide the directional information upon a request.

According to an aspect of the invention, the output audio stream 2470 as well as the output directional information stream 2441 is preferably in a digital form with a single audio stream and a metadata stream embedded or along the audio stream. However, the audio stream 2470 and the directional information stream 2441 may use different outputs. Further, while the audio stream 2470 and the directional information stream 2441 in some embodiments use the same transmission path, e.g. the same network, they may in alternative embodiments use different transmission paths. E.g., the audio stream 2470 may be transmitted via a wired network connection and the directional information stream 2441 may be transmitted wirelessly. In this case, measures need to be taken that enable a synchronization of the directional information stream 2441 with the audio stream 2470 at the receiving side, e.g. time stamps.

According to an aspect of the invention, beamforming is performed at the transmitting side 10 to generate a single de-reverberated audio signal which can be used at the receiving side 20 for a remote virtual audio rendering. According to an aspect of the invention, the microphone array at the transmitting side 10 can perform beamforming for one or more audio beams to create a single audio channel accommodating possibly multiple conference room talkers. This can be performed for example by directing the beams to separate talkers and multiplexing the audio signals from the different talkers with a synchronized metadata stream identifying the talkers' positions. The synchronized positional metadata information can be used by the binaural rendering engine 3200 at the receiving side 20 to place the talkers at respective specific virtual locations in the rendered audio environment. This can be done using a single audio channel or multiple audio channels.

According to an aspect of the invention, a delay compensation of the audio stream is performed for synchronizing the position metadata with the audio channel. The positional metadata timing can be characterized by real time measuring to determine network latency.

Moreover, an independent audio rendering and position updating method can be used to manage latency, position updates and audio rendering.

According to an aspect of the invention, a near field acoustic characteristic, like reverberation, can be measured at the transmitting side 10 and used to allow a rendering of the same virtual reverberation at the receiving side 20. The measurement of the far end acoustic characteristic (e.g. reverb) allows a rendering of the conference room talkers in an acoustic environment matching that at the receiving side.

When a microphone array with a conventional Delay-and-Sum Beamformer (DSB) is successively steered at points in space by adjusting its steering delays, the output power of the beamformer can be used as a measure indicating where a sound source is located. The steered response power (SRP) algorithm as described in U.S. Pat. No. 9,894,434 B2 performs this task in a different way, namely by calculating generalized cross correlations (GCC) between pairs of input signals and comparing them against a table of expected time difference of arrival (TDOA) values. If the signals of two microphones are practically time delayed versions of each other, which will be the case for two microphones picking up the direct path of a sound source in the far field, their GCC will have a distinctive peak at the position corresponding to the TDOA of the two signals and it will be close to zero for all other positions. SRP uses this property to calculate a score by summing the GCCs of a multitude of microphone pairs at the positions of expected TDOAs, each corresponding to a certain position in space. By successively repeating this summation over several points in space that are part of a pre-defined search grid, an SRP score is gathered for each point in space. The position with the highest SRP score is considered as the sound source position.

Figure 5:
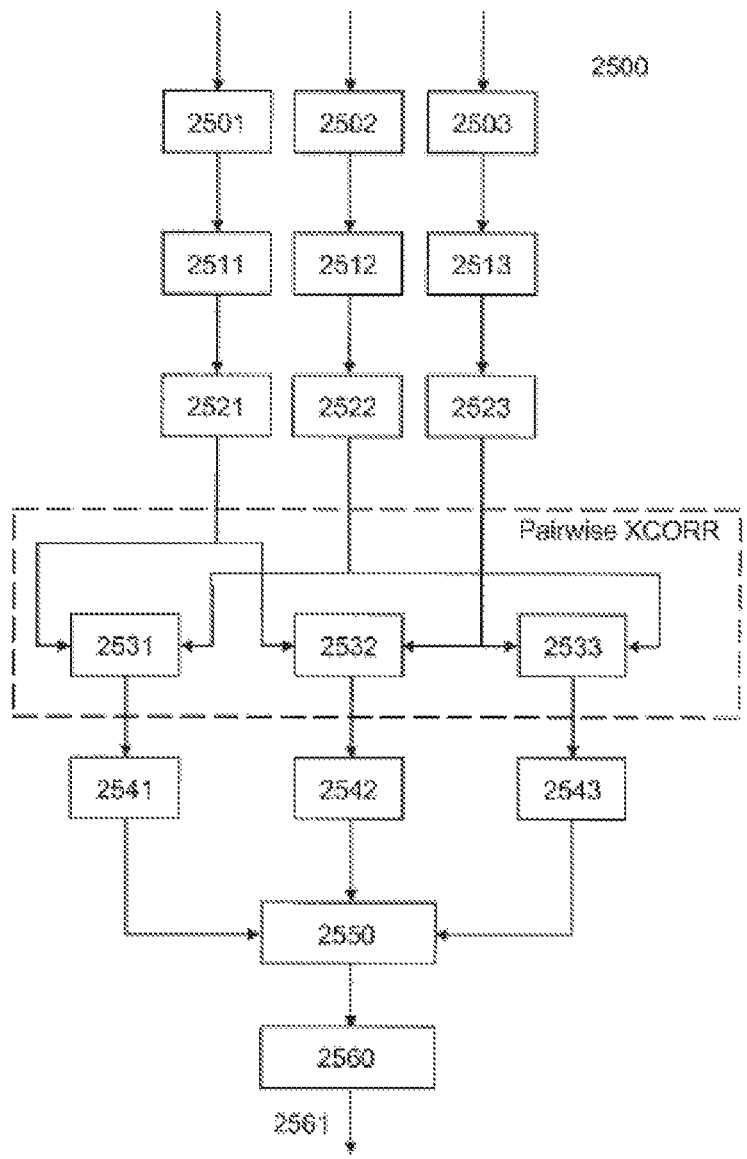
FIG. 5 shows the functional structure of the SRP-PHAT algorithm as implemented in the microphone system, in one embodiment.

FIG. 5 shows the functional structure of the SRP-PHAT algorithm that may be implemented in one embodiment of the microphone array unit. At the top, only three input signals are shown that stand as placeholders for the plurality of input signals fed to the algorithm. The cross correlation can be performed in the frequency domain. Therefore, blocks of digital audio data from a plurality of inputs are each multiplied by an appropriate window 2501-2503 to avoid artifacts and then transformed into the frequency domain 2511-2513. The block length directly influences the detection performance. Longer blocks achieve better detection accuracy of position-stationary sources, while shorter blocks allow for more accurate detection of moving sources and less delay. Preferably the block length is set to a value so that each part of spoken words can be detected fast enough while still being accurate in position. Thus, preferably a block length of about 20-100 ms is used.

Afterwards, the phase transform 2521-2523 and pairwise cross-correlation of signals 2531-2533 is performed before transforming the signals into the time domain again 2541-2543. These GCCs are then fed into the scoring unit 2550. The scoring unit computes a score for each point in space on a pre-defined search grid. The position in space that achieves the highest score is considered to be the sound source position.

By using a phase transform weighting for the GCCs, the algorithm can be made more robust against reflections, diffuse noise sources and head orientation. In the frequency domain, the phase transform as performed in the units 2521-2523 divides each frequency bin with its amplitude, leaving only phase information. In other words, the amplitudes are set to 1 for all frequency bins.

The SRP-PRAT algorithm can be further improved, as described in the prior art.

In a typical SRP-PHAT scenario, the signals of all microphone capsules of an array will be used as inputs to the SRP-PHAT algorithm, all possible pairs of these inputs will be used to calculate GCCs and the search grid will be densely discretizing the space around the microphone array. All this leads to very high amounts of processing power required for the SRP-PHAT algorithm.

For reducing the required processing power without sacrificing for detection precision, it is possible to choose only a set of microphones as inputs to the algorithm or particular microphone pairs to calculate GCCs of. By choosing microphone pairs that give good discrimination of points in space, the processing power can be reduced while keeping the detection precision high.

As the microphone system only requires a look direction to point to a source, it is further not desirable to discretize the whole space around the microphone array into a search grid, as distance information is not necessarily needed. If a hemisphere with a radius much larger than the distance between the microphone capsules used for the GCC pairs is used, it is possible to detect the direction of a source very precisely, while at the same time reducing the processing power significantly, as only a hemisphere search grid is to be evaluated. Furthermore, the search grid is independent from room size and geometry and risk of ambiguous search grid positions e.g. if a search grid point would be located outside of the room. Therefore, this solution is also advantageous for prior art solutions to reduce the processing power like coarse to fine grid refinement, where first a coarse search grid is evaluated to find a coarse source position and afterwards the area around the detected source position will be searched with a finer grid to find the exact source position.

It can be desirable to also have distance information of the source, in order to e.g. adapt the beam width to the distance of the source so as to avoid a too narrow beam for sources close to the array or in order to adjust the output gain or the equalizing according to the distance of the source.

Figure 6A:
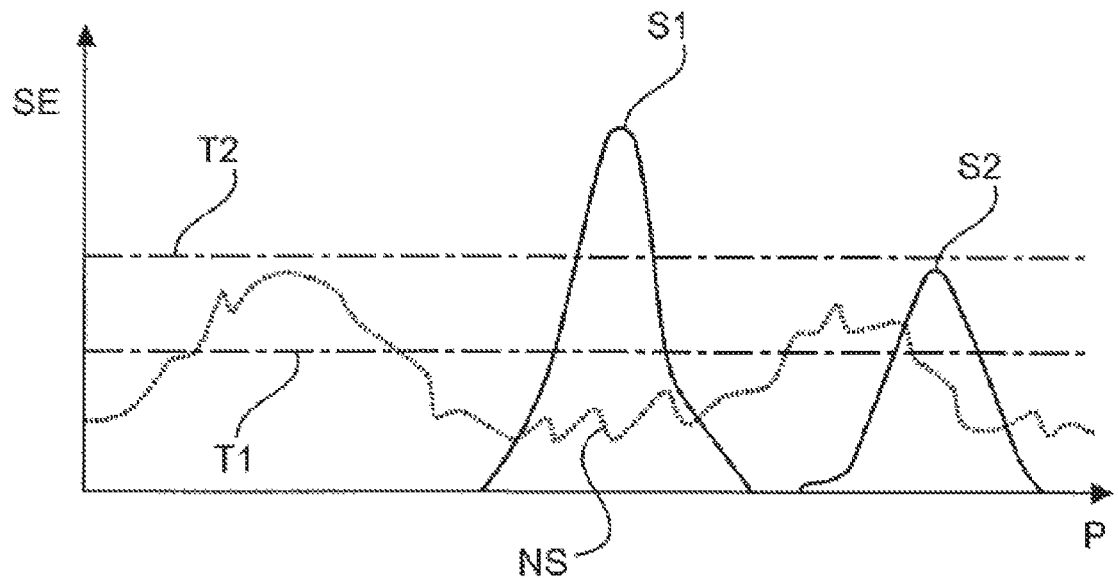
FIG. 6A shows a graph indicating a "silence mode" detection threshold based on sound energy.

Besides of significantly reducing the required processing power of typical SRP-PHAT implementations, the robustness against disturbing noise sources can be improved by a set of measures. If there is no person speaking in the vicinity of the microphone system and the only signals picked up are noise or silence, the SRP-PHAT algorithm will operate in a kind of "silence mode". In this mode, it will either detect a noise source as source position or, especially in the case of diffuse noises or silence, quasi randomly detect a "source" anywhere on the search grid. This either leads to predominant acquisition of noise or audible audio artifacts due to a beam randomly pointing at different positions in space with each block of audio. It is known from prior art that this problem can be solved to some extent by computing the input power of at least one of the microphone capsules and to only steer a beam if the input power is above a certain threshold. The disadvantage of this method is that the threshold has to be adjusted very carefully depending on the noise floor of the room and the expected input power of a speaking person. This requires interaction with the user or at least time and effort during installation. This known "silence mode" detection based on sound energy SE is depicted in FIG. 6A. Setting the sound energy threshold to a first threshold T1 results in noise being picked up, while the stricter threshold setting of a second threshold T2 misses a second source S2. Furthermore, input power computation requires some CPU usage, which is usually a limiting factor for automatically steered microphone array systems and thus needs to be saved wherever possible.

Figure 6B:
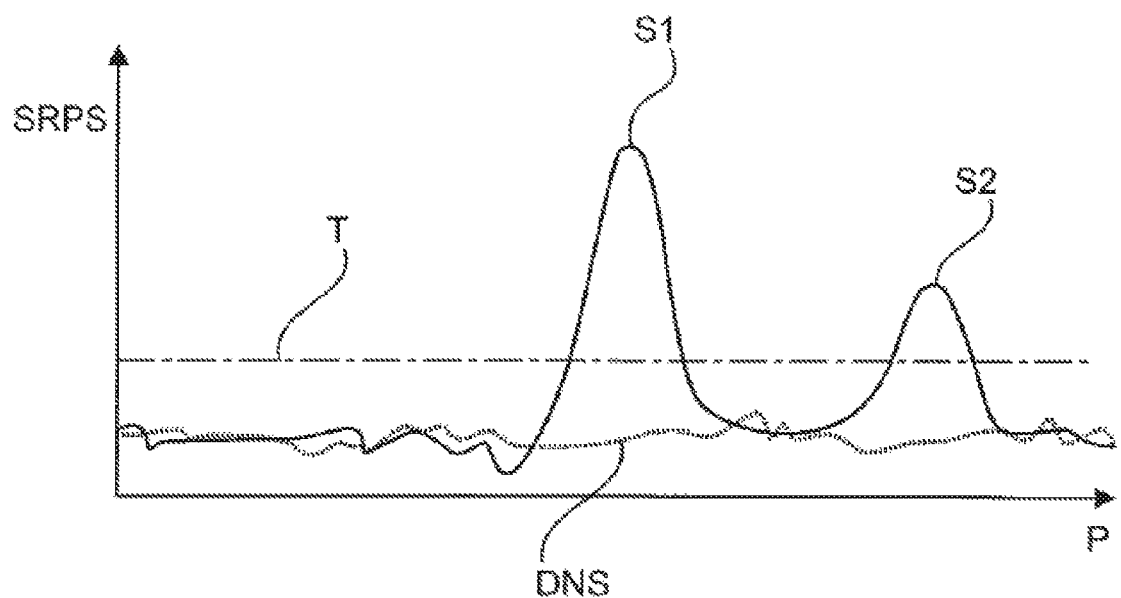
FIG. 6B shows a graph indicating a "silence mode" detection threshold based on an SRP-score.

The invention, in one embodiment, may overcome this problem by using the SRP-PHAT score that is already computed for the source detection as a threshold metric (SRP-threshold) instead or in addition to the input power. The SRP-PHAT algorithm is insensitive to reverberation and other noise sources with a diffuse character. In addition, most noise sources as e.g. air conditioning systems have a diffuse character while sources to be detected by the system usually have a strong direct or at least reflected sound path. Thus, most noise sources will produce rather low SRP-PHAT scores, while a speaking person will produce much higher scores. This is mostly independent of the room and installation situation and therefore no significant installation effort and no user interaction is required, while at the same time a speaking person will be detected, and diffuse noise sources will not be detected by the system. As soon as a block of input signals achieves an SRP-PHAT score of less than the threshold, the system can e.g. be muted, or the beam can be kept at the last valid position that gave a maximum SRP-PHAT score above the threshold. This avoids audio artifacts and detection of unwanted noise sources. The advantage of "silence mode" detection based on the SRP score (SRPS) over a detection based on sound energy is depicted in FIG. 6B. Mostly, diffuse noise sources produce a very low SRP score that is far below the SRP score of sources to be detected, even if they are rather subtle such as S2.

Thus, this gated SRP-PRAT algorithm is more robust against diffuse noise sources without the need of tedious setup and/or control by the user.

However, noise sources with a non-diffuse character that are present at the same or higher sound energy level as the wanted signal of a speaking person, might still be detected by the gated SRP-PHAT algorithm. Although the phase transform will result in frequency bins with uniform gain, a noise source with high sound energy will still dominate the phase of the systems input signals and thus lead to predominant detection of such sources. These noise sources can for example be projectors mounted closely to the microphone system or sound reproduction devices used to play back the audio signal of a remote location in a conference scenario. In one embodiment, the invention may make use of the pre-defined search grid of the SRP-PHAT algorithm to avoid detection of such noise sources. If areas are excluded from the search grid, these areas are hidden for the algorithm and no SRP-PHAT score will be computed for these areas. Therefore, no noise sources situated in such a hidden area can be detected by the algorithm. Especially in combination with the introduced SRP-threshold this is a very powerful solution to make the system robust against noise sources.

Figure 7A:
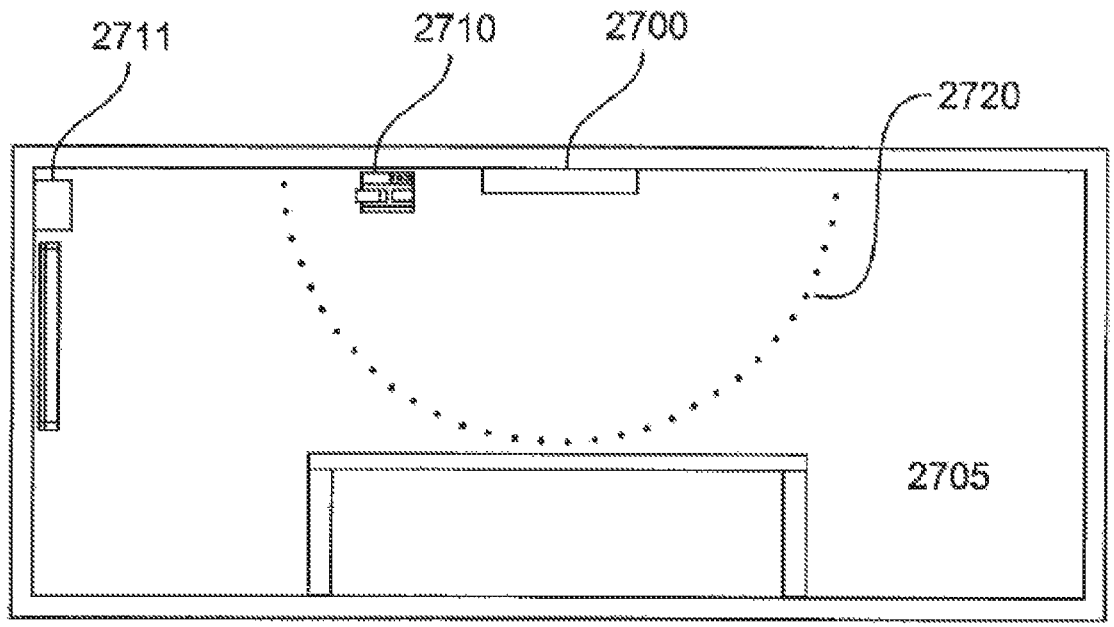
FIG. 7A shows a schematic representation of a conference room according to an example.
Figure 7B:
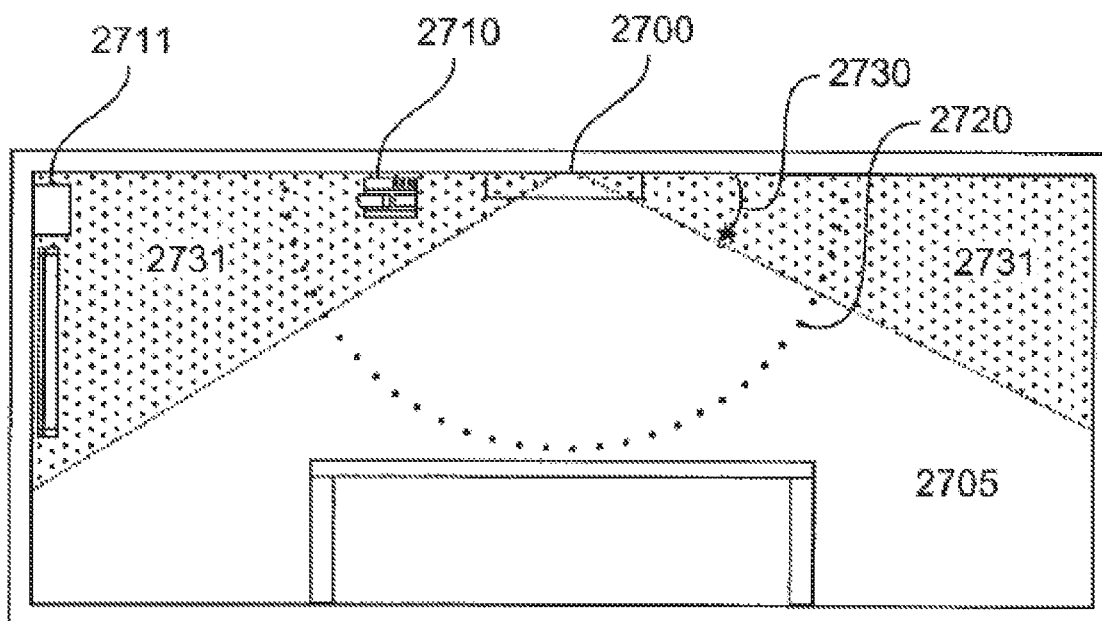
FIG. 7B shows a schematic representation of a conference room according to the invention.

FIG. 7A shows a schematic representation of a conference room 2705 with a microphone system 2700 that uses an unrestrained search grid. The above-described SRP scores are calculated using search grid points 2720. In a first mode shown in FIG. 7A, all depicted search grid points 2720 are used. FIG. 7B shows a schematic representation of the same conference room with the microphone system 2700 in a second mode where it uses exclusion sectors 2731, according to one embodiment of the invention.

In FIG. 7B, the exclusion of detection areas of the microphone system 2700 in the conference room 2705 is achieved by defining an angle 2730 that creates an exclusion sector 2731 where no active search grid points 2720 are located. This can be achieved by deactivating the respective search grid points that are located within the angle 2730. Disturbing sources are typically located either under the ceiling, like a projector 2710, or on elevated positions at the walls of the room, like sound reproduction devices 2711. Thus, these noise sources will be within the exclusion sector and will not be detected by the system. The exclusion sector 2731 has not only an elevation angle, like angle 2730 in FIG. 7, but also an azimuth angle, i.e. an angle around a vertical axis. The azimuth angle can be up to 360°. For smaller azimuth angles, also multiple exclusion sectors 2731 are possible, e.g. a first exclusion sector at 15°-25° and a second exclusion sector at 165°-170°. These may have different azimuth angle widths and/or different elevation angles.

The exclusion of a sector of the hemispherical search grid is the preferred solution as it covers most noise sources without the need of defining each noise sources position. This is an easy way to hide noise sources with directional sound radiation while at the same time ensure detection of speaking persons. Furthermore, it is possible to leave out specific areas where a disturbing noise source is located, and the exclusion may be programmed and re-programmed flexibly.

In one embodiment, the invention solves a problem that appears if the exclusion of certain areas is not feasible, e.g. if noise sources and speaking persons are located very close to each other. Many disturbing noise sources have most of their sound energy SE in certain frequency ranges, as depicted in FIG. 8. In such a case, a disturbing noise source NS can be excluded from the source detection algorithm by masking certain frequency ranges 2820 in the SRP-PHAT algorithm. This can be achieved by setting the appropriate frequency bins to zero and only keeping information in a range 2810 of the frequency band where most source frequency information is located. This may be performed in the phase transform units 2521-2523. This is especially useful for low frequency noise sources.

But even taken alone this technique is very powerful to reduce the chance of noise sources being detected by the source recognition algorithm. Dominant noise sources with a comparably narrow frequency band can be suppressed by excluding the appropriate frequency band from the range of SRP frequencies SRPF that are used for source detection. Broadband low frequency noise can also be suppressed very well, as speech has a very wide frequency range and the source detection algorithms as presented works very robust even when only making use of higher frequencies.

Combining the above techniques allows for a manual or automated setup process, where noise sources are detected by the algorithm and either successively removed from the search grid, masked in the frequency range and/or hidden by locally applying a higher SRP-threshold.

SRP-PHAT detects a source for each frame of audio input data, independently from sources previously detected. This characteristic allows the detected source to suddenly change its position in space. This is a desired behavior if there are two sources reciprocally active shortly after each other and allows instant detection of each source. However, sudden changes of the source position might cause audible audio artifacts if the array is steered directly using the detected source positions, especially in situations where e.g. two sources are concurrently active. Furthermore, it is not desirable to detect transient noise sources such as placing a coffee cup on a conference table or a coughing person.

Therefore the source detection unit may make use of different known smoothing techniques in order to ensure an output that is free from audible artifacts caused by a rapidly steered beam and robust against transient noise sources while at the same time keeping the system fast enough to acquire speech signals without loss of intelligibility.

The signals captured by a multitude or array of microphones can be processed such that the output signal reflects predominant sound acquisition from a certain look direction, while not being sensitive to sound sources of other directions not being the look direction. The resulting directivity response is called the beam pattern, the directivity around the look direction is called beam, and the processing done in order to form the beam is the beamforming.

One way to process the microphone signals to achieve a beam is a Delay-and-sum beamformer (DSB). It sums all the microphone's signals after applying individual delays for the signal captured by each microphone.

Since a Delay-and-sum beamformer (DSB) is known to have several drawbacks, a Filter-and-sum beamformer may be used instead. In a Filter-and-sum beamformer (FSB) the individual microphone signals are not just delayed and summed but, more generally, filtered with a transfer function and then summed. A Filter-and-sum beamformer allows for more advanced processing to overcome some of the disadvantages of a simple Delay-and-sum beamformer.

In one exemplary embodiment, an audio reproduction system for use in a conference system comprises a first interface unit adapted for receiving a single channel audio signal to be reproduced, a second interface unit adapted for receiving a directional signal, a processing unit and an audio reproduction unit. The single audio signal comprises sound acquired from an audio source in a first direction, and the directional signal comprises directional information defining the first direction. The processing unit is adapted for processing the received audio signal based on the directional signal, wherein a spatial audio signal is obtained. E.g., the processing unit may be implemented by one or more microprocessors that may be configured accordingly by software, and may comprise a binaural rendering engine for providing the spatial audio signal. The audio reproduction unit is adapted for spatially reproducing the spatial audio signal.

In one embodiment, the audio reproduction system further comprises a reverberation simulation unit adapted for performing a reverberation processing on the received audio signal, as described above. The spatial audio signal is reproduced with a simulated reverberation.

In one embodiment, the reverberation simulation unit uses for the reverberation processing parameters locally provided to the audio reproduction system. In another embodiment, the reverberation simulation unit uses for the reverberation processing parameters received via the second interface unit and provided at a transmitting side. In one embodiment, the audio reproduction system further comprises a third interface unit for sending requests, and the directional signal is received upon a sent request. The first, second and third interface units may be different interface units, or they may be of the same type or even identical The microphone system according to the invention allows not only for predominant sound acquisition of the desired audio source, e.g. a person talking, utilizing microphone array signal processing, but also for immersive reproduction of the acquired sound. In certain environments like very large rooms and thus very long distances of the source location to the microphone system or very reverberant situations, it might be desirable to have even better sound pickup. Therefore, it is possible to combine more than one of the microphone systems in order to form a multitude of microphone arrays. Preferably each microphone is calculating a single beam and an automixer selects one or mixes several beams to form the output signal. An automixer is available in most conference system processing units and provides the simplest solution to combine multiple arrays. Other techniques to combine the signal of a multitude of microphone arrays are possible as well. For example, the signal of several line and or planar arrays could be summed. Also, different frequency bands could be taken from different arrays to form the output signal (volumetric beamforming).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims. For example, the microphone array unit may comprise its plurality of microphone capsules arranged in or on a board mountable on a wall, in a camera or in a portable appliance.

The invention claimed is:

1. A conference system, comprising:
   at a transmitting side:
   a microphone array unit having a plurality of microphone capsules arranged in or on a board mountable on or in a ceiling of a conference room; and
   a processing unit that is configured to receive output signals of the microphone capsules and to execute audio beamforming based on the received output signals of the microphone capsules for predominantly acquiring sound coming from an audio source in a first direction, wherein the processing unit comprises:
     a direction recognition unit that is configured to compute from the output signals of said microphone capsules a score for each of a plurality of spatial positions on a search grid and use a search grid spatial position having a higher score than that of one or more of the other search grid spatial positions to identify said first direction,
     wherein the direction recognition unit is further configured to determine a distance information from the output signals of said microphone capsules; and
   at a receiving side:
   an audio reproduction system configured to reproduce the audio signal detected by the microphone array with directional information of the first direction, the directional information comprising said distance information;
   wherein an audio signal detected by the microphone capsules as well as said directional information regarding the first direction is transmitted from the transmitting side to the receiving side, the directional information comprising said distance information.

2. The conference system according to claim 1;
wherein the processing unit is configured to control the microphone array to exclude at least one predetermined exclusion sector in which a noise source is located from processing, the exclusion sector corresponding to at least one predetermined spatial position in the search grid; and
wherein the direction recognition unit is further configured to compare scores of different spatial positions of the search grid and to output a directional signal indicating said first direction.

3. The conference system according to claim 2;
wherein the at least one predetermined spatial position of the search grid corresponding to the exclusion sector is excluded from at least one of said computing and said comparing.

4. The conference system according to claim 1;
wherein the direction recognition unit is configured to compute said score for each of a plurality of spatial positions on a search grid from outputs of only a subset of said microphone capsules.

5. The conference system according to claim 4;
wherein said subset of microphone capsules comprises at least two microphone capsules, and wherein at least one microphone capsule of the microphone array unit is not included in the subset of microphone capsules.

6. The conference system according to claim 1;
wherein the direction recognition unit is configured to use said search grid spatial position having a highest score to identify said first direction only when said highest score is above a predefined threshold.

7. The conference system according to claim 1;
wherein the direction recognition unit is configured to periodically re-compute the scores for the spatial positions of the search grid, re-identify a search grid position having a highest score and to re-adjust the audio beamforming accordingly.

8. The conference system according to claim 1;
wherein the audio reproduction system at the receiving side is configured to reproduce the transmitted audio signal with said directional information with a simulated reverberation.

9. The conference system according to claim 8;
wherein the simulated reverberation is a reverberation of a room at the transmitting side in which the microphone array unit is positioned, or the simulated reverberation is a reverberation of a room at the receiving side in which the audio signal is reproduced.

10. The conference system according to claim 1;
wherein, at the transmitting side, the distance information of the directional information is utilized for adapting a width of an audio beam generated by said audio beam forming to a distance between the microphone array and the audio source.

11. The conference system according to claim 1;
wherein, at the receiving side, the distance information of the directional information is utilized for audio rendering.

12. A method of controlling a conference system having at a transmitting side a microphone array unit having a plurality of microphone capsules arranged in or on a board mountable on or in a ceiling of a conference room and at a receiving side an audio reproduction system, comprising the steps of:
   at the transmitting side:
   detecting a direction and a distance of an audio source based on output signals of the microphone array unit;
   providing a direction signal defining the detected direction and distance;
   performing an audio beamforming towards said detected direction to detect audio signals;

transmitting said detected audio signals to the receiving side;
transmitting directional information including said detected direction and distance to the receiving side; and
at the receiving side:
reproducing said transmitted audio signal with the transmitted directional information.

13. The method of claim 12;
further comprising steps of:
forming a synchronous metadata stream comprising said directional information; and
providing said synchronous metadata stream at an output for said transmitting.

14. The method of claim 12;
further comprising steps of:
receiving a request on an input; and
in response to said request, providing said directional information at an output for said transmitting.

15. The method of claim 12;
wherein the step of detecting a direction comprises computing a score for each of a plurality of spatial positions on a search grid from outputs of at least a subset of said microphone capsules.

16. The method of claim 15;
wherein each score defines a sum of cross-correlation values of output signals of pairs of the microphone capsules using a specified delay that corresponds to a direction towards the respective spatial position.

17. The method of claim 15;
wherein said score is computed from the received output signals of only a subset of said microphone capsules, and the audio beamforming is based on the received output signal of all said microphone capsules.

18. The method of claim 12;
wherein, at the transmitting side, the distance is utilized for adapting a width of an audio beam generated by said audio beam forming to a distance between the microphone array and the audio source.

19. The method of claim 12;
wherein, at the receiving side, the distance included in the directional information is utilized for audio rendering.

20. A microphone array unit for use in a conference system, the microphone array unit comprising:
a plurality of microphone capsules arranged in or on a board mountable on or in a ceiling of a conference room; and
a processing unit that is configured to receive output signals of the microphone capsules and to execute audio beamforming based on the received output signals of the microphone capsules for predominantly acquiring sound coming from an audio source in a first direction, wherein the processing unit comprises:
a direction recognition unit that is configured to compute from the output signals of said microphone capsules a score for each of a plurality of spatial positions on a search grid and use a search grid spatial position having a higher score than that of one or more of the other search grid spatial positions to identify said first direction,
wherein the direction recognition unit is further configured to determine a distance information from the output signals of said microphone capsules;
wherein the microphone array unit provides at an output an audio signal detected by the microphone capsules, the audio signal comprising said acquired sound coming from an audio source in the first direction, and
wherein the microphone array unit further provides at the output directional information regarding the first direction at an output for transmission to a receiving side, the directional information further comprising said distance information.

21. The microphone array unit of claim 20;
wherein the directional information is provided as a synchronous metadata stream.

22. The microphone array unit of claim 20;
wherein the microphone array unit further comprises an input configured to receive requests, and wherein the directional information is provided upon a request.

23. The microphone array unit of claim 20;
wherein the direction recognition unit is configured to compute said score for each of a plurality of spatial positions on a search grid from outputs of only a subset of said microphone capsules.

24. The microphone array unit of claim 20;
wherein the distance information of the directional information is utilized for adapting a width of an audio beam generated by said audio beamforming to a distance between the microphone array and the audio source.

25. An audio reproduction system for use in a conference system, the audio reproduction system comprising:
a first interface unit configured to receive a single channel audio signal to be reproduced, wherein the single channel audio signal comprises sound acquired by a microphone array from an audio source in a first direction;
a second interface unit configured to receive a directional signal, wherein the directional signal comprises directional information defining the first direction and a distance information defining a distance between said audio source and said microphone array;
a processing unit configured to process the received audio signal based on the directional information and distance information of said directional signal, the processing unit comprising a binaural rendering engine and being configured to provide a spatial audio signal; and
an audio reproduction unit configured to spatially reproduce the spatial audio signal.

26. The audio reproduction system according to claim 25;
further comprising a reverberation simulation unit configured to perform a reverberation processing on the received audio signal, wherein the spatial audio signal is reproduced with a simulated reverberation.

27. The audio reproduction system according to claim 26;
wherein, for the reverberation processing, the reverberation simulation unit is configured to utilize parameters locally provided to the audio reproduction system.

28. The audio reproduction system according to claim 26;
wherein, for the reverberation processing, the reverberation simulation unit is configured to utilize parameters received via the second interface and provided at a transmitting side.

29. The audio reproduction system according to claim 25,
further comprising:
a third interface unit configured to send requests, wherein the directional signal is received upon a sent request.

30. A conference system, comprising:
at a transmitting side:
a microphone array unit having a plurality of microphone capsules arranged in or on a board mountable on or in a ceiling of a conference room; and
a processing unit that is configured to receive output signals of the microphone capsules and to execute audio beamforming based on the received output signals of the microphone capsules for predominantly acquiring sound coming from an audio source in a first direction,
wherein the processing unit is further configured to control the microphone array to exclude from processing at least one predetermined exclusion sector, the exclusion sector corresponding to at least one programmable spatial position in a search grid; and
wherein the processing unit comprises:
a direction recognition unit that is configured to compute from the output signals of said microphone capsules a score for each of a plurality of spatial positions on the search grid and use a search grid spatial position having a higher score than that of one or more of the other search grid spatial positions to identify said first direction; and
at a receiving side:
an audio reproduction system configured to reproduce the audio signal detected by the microphone array with directional information of the first direction;
wherein an audio signal detected by the microphone capsules as well as said directional information regarding the first direction is transmitted from the transmitting side to the receiving side.

31. The conference system according to claim 30, wherein the processing unit is configured to enable flexible re-programming said at least one spatial position in the search grid, wherein the at least one exclusion sector is modified.

32. A microphone array unit for use in a conference system, the microphone array unit comprising:
a plurality of microphone capsules arranged in or on a board mountable on or in a ceiling of a conference room; and
a processing unit that is configured to receive output signals of the microphone capsules and to execute audio beamforming based on the received output signals of the microphone capsules for predominantly acquiring sound coming from an audio source in a first direction,
wherein the processing unit is further configured to control the microphone array to exclude at least one predetermined exclusion sector from processing, the exclusion sector corresponding to at least one programmable spatial position in a search grid; and
wherein the processing unit comprises:
a direction recognition unit that is configured to compute from the output signals of said microphone capsules a score for each of a plurality of spatial positions on the search grid and use a search grid spatial position having a higher score than that of one or more of the other search grid spatial positions to identify said first direction;
wherein the microphone array unit provides at an output an audio signal detected by the microphone capsules, the audio signal comprising said acquired sound coming from an audio source in the first direction, and wherein the microphone array unit further provides at the output directional information regarding the first direction at an output for transmission to a receiving side.

33. The microphone array unit according to claim 32, wherein the processing unit is configured to enable flexible re-programming said at least one spatial position in the search grid, wherein the at least one exclusion sector is modified.

* * * * *